United States Patent
Gillespie, III

(10) Patent No.: US 7,736,333 B2
(45) Date of Patent: *Jun. 15, 2010

(54) AUTOMATIC MIXING AND INJECTING APPARATUS

(75) Inventor: Richard D. Gillespie, III, Athens, TX (US)

(73) Assignee: West Pharmaceutical Services of Delaware, Inc., Lionville, PA (US)

( * ) Notice: Subject to any disclaimer, the term of this patent is extended or adjusted under 35 U.S.C. 154(b) by 1483 days.

This patent is subject to a terminal disclaimer.

(21) Appl. No.: 10/601,212

(22) Filed: Jun. 20, 2003

(65) Prior Publication Data

US 2004/0054327 A1  Mar. 18, 2004

Related U.S. Application Data

(63) Continuation of application No. PCT/US01/50102, filed on Dec. 21, 2001, which is a continuation of application No. 09/745,905, filed on Dec. 21, 2000, now Pat. No. 6,387,078.

(51) Int. Cl.
*A61M 5/00* (2006.01)
*A61M 5/14* (2006.01)
*A61M 5/20* (2006.01)
*A61M 5/24* (2006.01)
*A61M 5/28* (2006.01)

(52) U.S. Cl. .................... 604/110; 604/87; 604/135; 604/201

(58) Field of Classification Search ............... 604/181, 604/191, 200–207, 264, 82–92, 110, 134–139, 604/156, 157, 192, 197, 198
See application file for complete search history.

(56) References Cited

U.S. PATENT DOCUMENTS

| 2,717,601 A | * | 9/1955 | Brown ...................... 206/221 |
| 3,306,290 A | | 2/1967 | Weltman |
| 3,572,336 A | | 3/1971 | Hershberg |

(Continued)

FOREIGN PATENT DOCUMENTS

EP        0288443 B1   9/1992

(Continued)

OTHER PUBLICATIONS

A Supplementary Partial European Search Report for the corresponding European Patent Application No. 01 99 2319; Date of completion of the search: Aug. 5, 2008; 3 pages.

(Continued)

*Primary Examiner*—Nicholas D Lucchesi
*Assistant Examiner*—Nathan R Price
(74) *Attorney, Agent, or Firm*—Panitch Schwarze Belisario & Nadel LLP

(57) ABSTRACT

An automatic mixing and injecting apparatus comprises a syringe assembly (400) within a housing (100). The syringe assembly (400) has a chamber (425) for holding a liquid, which can be a liquid medicine or a solvent. A second chamber (460) may hold a dry medicine. The second chamber (460) is releasably sealed with respect to the first chamber (425). A spring-operated plunger (300) forces liquid from the first chamber (425) and causes the releasable seal (430) to disengage when the needle (540) has entered the recipient. At this time, the liquid flows through the second chamber (460) and dissolves any dry medicine in that chamber (460). A releasable coupling (340) disengages the plunger (300) from the driver spring (500) and allows the plunger (300), syringe assembly (400), and needle (540) to retract under the urging of a return spring (505).

26 Claims, 9 Drawing Sheets

U.S. PATENT DOCUMENTS

| | | | |
|---|---|---|---|
| 4,059,109 A | | 11/1977 | Tischlinger |
| 4,592,745 A | * | 6/1986 | Rex et al. .................... 604/211 |
| 4,613,326 A | | 9/1986 | Szwarc |
| D286,164 S | | 10/1986 | Tinz |
| D287,603 S | | 1/1987 | Bruhn |
| 4,643,721 A | | 2/1987 | Brunet |
| 4,689,042 A | | 8/1987 | Sarnoff et al. |
| 4,755,169 A | | 7/1988 | Sarnoff et al. |
| 4,820,286 A | * | 4/1989 | van der Wal .................. 604/89 |
| 4,822,340 A | | 4/1989 | Kamstra |
| 4,898,580 A | | 2/1990 | Crowley |
| 4,969,877 A | | 11/1990 | Kornberg |
| 4,998,922 A | | 3/1991 | Kuracina et al. |
| 5,085,641 A | | 2/1992 | Sarnoff et al. |
| 5,085,642 A | | 2/1992 | Sarnoff et al. |
| 5,092,843 A | | 3/1992 | Monroe et al. |
| 5,102,393 A | | 4/1992 | Sarnoff et al. |
| 5,120,310 A | | 6/1992 | Shaw |
| 5,188,613 A | | 2/1993 | Shaw |
| D339,606 S | | 9/1993 | Podobrin |
| 5,267,961 A | | 12/1993 | Shaw |
| 5,295,965 A | | 3/1994 | Wilmot |
| 5,300,030 A | | 4/1994 | Crossman et al. |
| 5,358,489 A | | 10/1994 | Wyrick |
| 5,364,363 A | | 11/1994 | Pearson et al. |
| 5,383,865 A | | 1/1995 | Michel |
| 5,385,551 A | | 1/1995 | Shaw |
| 5,389,076 A | | 2/1995 | Shaw |
| 5,391,151 A | | 2/1995 | Wilmot |
| 5,423,758 A | | 6/1995 | Shaw |
| 5,425,715 A | | 6/1995 | Dalling et al. |
| 5,540,664 A | | 7/1996 | Wyrick |
| 5,545,145 A | | 8/1996 | Clinton et al. |
| 5,578,011 A | | 11/1996 | Shaw |
| 5,584,815 A | * | 12/1996 | Pawelka et al. ............. 604/191 |
| 5,599,309 A | | 2/1997 | Marshall |
| 5,620,421 A | | 4/1997 | Schmitz |
| 5,626,566 A | * | 5/1997 | Petersen et al. ............. 604/208 |
| 5,632,733 A | | 5/1997 | Shaw |
| 5,637,092 A | | 6/1997 | Shaw |
| 5,643,214 A | | 7/1997 | Marshall et al. |
| 5,665,071 A | | 9/1997 | Wyrick |
| 5,674,204 A | | 10/1997 | Chanoch |
| 5,685,846 A | | 11/1997 | Michaels, Jr. |
| 5,688,251 A | * | 11/1997 | Chanoch .................... 604/208 |
| 5,695,472 A | | 12/1997 | Wyrick |
| 5,779,677 A | | 7/1998 | Frezza |
| 5,779,679 A | | 7/1998 | Shaw |
| 5,810,775 A | | 9/1998 | Shaw |
| 5,817,058 A | | 10/1998 | Shaw |
| 5,820,602 A | * | 10/1998 | Kovelman et al. ........... 604/187 |
| RE35,986 E | | 12/1998 | Ritson et al. |
| 5,873,462 A | | 2/1999 | Nguyen et al. |
| 5,921,966 A | * | 7/1999 | Bendek et al. ............. 604/207 |
| 5,931,817 A | | 8/1999 | Nguyen et al. |
| 5,941,857 A | | 8/1999 | Nguyen et al. |
| 5,944,700 A | | 8/1999 | Nguyen et al. |
| D414,201 S | | 9/1999 | Larson et al. |
| 5,957,896 A | | 9/1999 | Bendek et al. |
| 5,957,897 A | | 9/1999 | Jeffrey |
| D414,807 S | | 10/1999 | Baudino et al. |
| 5,961,495 A | | 10/1999 | Walters et al. |
| 5,989,220 A | | 11/1999 | Shaw et al. |
| 5,997,512 A | | 12/1999 | Shaw |
| 6,001,082 A | | 12/1999 | Dair et al. |
| 6,015,438 A | | 1/2000 | Shaw |
| D423,577 S | | 4/2000 | Baudino et al. |
| D425,120 S | | 5/2000 | Ramil |
| 6,086,563 A | | 7/2000 | Moulton et al. |
| 6,099,503 A | | 8/2000 | Stradella |
| 6,210,371 B1 | | 4/2001 | Shaw et al. |
| 6,221,046 B1 | | 4/2001 | Burroughs et al. |
| 6,221,053 B1 | | 4/2001 | Walters et al. |
| 6,221,055 B1 | | 4/2001 | Shaw et al. |
| D441,398 S | | 5/2001 | Owen et al. |
| 6,241,709 B1 | * | 6/2001 | Bechtold et al. ............. 604/207 |
| 6,248,095 B1 | | 6/2001 | Giambattista et al. |
| D446,242 S | | 8/2001 | Stukenkemper |
| 6,277,099 B1 | | 8/2001 | Strowe et al. |
| D452,271 S | | 12/2001 | Owen et al. |
| 6,346,094 B2 | | 2/2002 | West et al. |
| 6,387,078 B1 | * | 5/2002 | Gillespie, III ............... 604/181 |
| 6,428,528 B2 | * | 8/2002 | Sadowski et al. ........... 604/511 |
| 6,494,863 B1 | | 12/2002 | Shaw et al. |
| 6,572,584 B1 | | 6/2003 | Shaw et al. |
| 6,793,646 B1 | | 9/2004 | Giambattista et al. |
| 7,097,634 B2 | * | 8/2006 | Gilbert ....................... 604/150 |
| 2003/0083621 A1 | | 5/2003 | Shaw et al. |
| 2003/0088216 A1 | | 5/2003 | Py |

FOREIGN PATENT DOCUMENTS

| | | |
|---|---|---|
| JP | 62270169 A | 11/1987 |
| JP | 3047750 U | 2/1998 |
| JP | 10507935 T | 8/1998 |
| JP | 2000316973 | 11/2000 |
| WO | 8802265 A1 | 4/1988 |
| WO | 9409839 A1 | 5/1994 |
| WO | WO9535126 | 6/1995 |

OTHER PUBLICATIONS

Examiner's First Report on related Australian Patent Appl 2002232782, dated May 20, 2005.
International Search Report for related International Application No. PCT/US01/50102; dated Jul. 11, 2002.
Written Opinion for related International Application No. PCT/US01/50102 dated Apr. 14, 2003.
Third Office Action issued for related Chinese Appl. No. 018221734, dated Jun. 6, 2008.
Second Office Action for related Chinese Patent Appl. No. 018221734, dated Feb. 22, 2008.
First Office Action for related Chinese Patent Appl. No. 018221734, dated Jan. 21, 2005.
Office Action issued for related Mexican Patent Appl. PA/A/2003/005614, dated Feb. 12, 2007.
Supplementary Partial European Search Report for related EP Patent Appl. 01992319, dated Aug. 5, 2008.
International Preliminary Examination Report for related International Application No. PCT/US01/50102, dated Sep. 22, 2003.
A Japanese First Office Action for the corresponding Japanese Patent Application No. 2002-551028; mailed May 17, 2005; 9 pages (including English translation).
A Japanese Second Office Action for the corresponding Japanese Patent Application No. 2002-551028; mailed Mar. 28, 2006; 6 pages (including English translation).
A Japanese Appeal Decision of Rejection for the corresponding Japanese Patent Application No. 2002-551028; mailed Nov. 11, 2008; 13 pages.

* cited by examiner

Fig. 3A
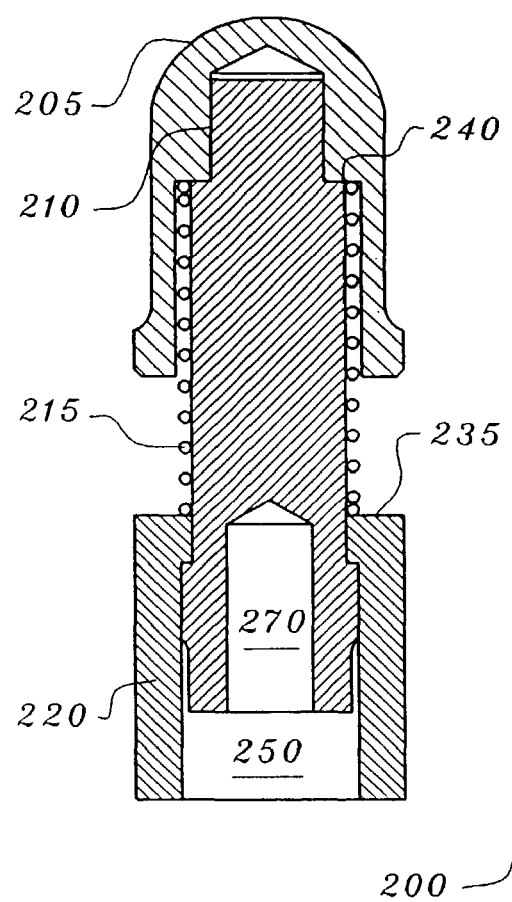
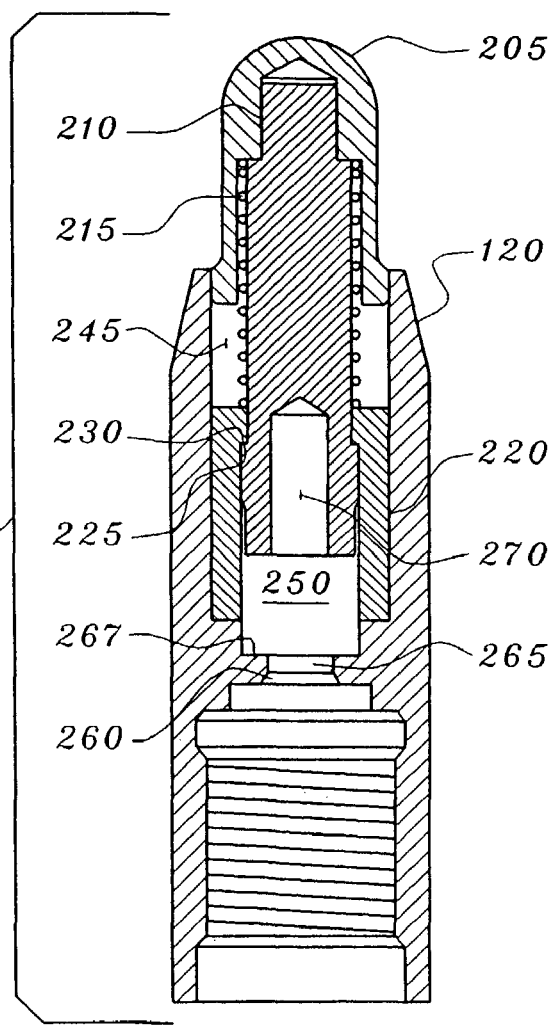
Fig. 3B

AUTOMATIC MIXING AND INJECTING APPARATUS

CROSS REFERENCE TO RELATED APPLICATIONS

This application is a continuation of PCT Application Serial No. PCT/US01/50102 filed on Dec. 21, 2001, which is a continuation of U.S. application Ser. No. 09/745,905 filed on Dec. 21, 2000, which issued on May 14, 2002 as U.S. Pat. No. 6,387,078, the contents of which are incorporated by reference herein.

CLAIM FOR PRIORITY

This application claims the benefit of the filing date of that certain U.S. patent application disclosing the same invention, titled "Automatic Mixing and Injecting Apparatus" and filed Dec. 21, 2001 under application Ser. No. 09/745,905.

TECHNICAL FIELD

The present invention relates to devices pre-loaded with a medicine and intended to automatically administer a pre-determined dose of a liquid medicine by means of an intra-muscular, subcutaneous or transdermal injection.

BACKGROUND ART

In particular, the present invention incorporates a number of important improvements and features as compared to the prior art, including enhanced functionality, convenience, safety and versatility. The present invention also provides a means for quickly administering a predetermined dose of medication when a need for rapid emergency treatment arises. The present invention may be embodied in a device that can be easily, safely and conveniently carried on the person. The present invention allows a single embodiment that may administer a liquid medicine alone or, alternatively, allow a liquid solvent to automatically mix with a dry medicine upon actuation of the device and concurrent with the injection process. The preferred embodiment automatically renders itself safe for disposal after use and eliminates the risk of injury to others through inadvertent contact with the used hypodermic needle. The recipient before, during, or after the injection, need not even see the hypodermic needle.

The use of automatic injection devices has been primarily reserved to emergency, life-sustaining situations. Additional applications for the present invention would be instances where the anatomical site of the injection, such as the penis, make the functional and psychological benefits associated with the use of such a device worth the added cost as compared to the conventional syringes.

There are numerous embodiments of automatic injection apparatuses in the prior art, e.g. Wyrick, U.S. Pat. No. 5,665,071; Schmitz, U.S. Pat. No. 5,620,421; and Wilmot, U.S. Pat. No. 5,295,965. None of the prior art patents provide all of the benefits of the present invention, however.

DISCLOSURE OF INVENTION

The present invention pertains to an automatic injection apparatus which injects a single, pre-measured dose of stored medicine intramuscularly or transdermally, and which automatically retracts the hypodermic needle into the device after the injection is completed. In the preferred embodiment, the medicine may comprise either a pre-prepared liquid medicine, a liquid solute that is forced through a dry drug chamber where a soluble medicine is mixed with the solute and carried in solution into the recipient, or a combination of a liquid medicine that also serves as a solute for a dry drug that mixes upon injection.

The preferred embodiment has an actuation end and a needle end. For the purposes of this application, the actuation end of the device will be referred to as the proximal end of the device and the needle end will be referred to as the distal end. The user presses the distal end of the device onto the desired injection site and presses the actuation button. This releases the plunger and syringe combination from its temporary engagement with the housing. The plunger and syringe combination is then forced away from the proximal end of the housing by a energized driver spring. The driver spring propels the plunger and syringe combination forward through the bore of the housing until the hypodermic needle exits the housing, and enters the recipient's tissue. During this movement, a return spring positioned between the syringe assembly and the fixed, distal end of the housing becomes compressed and energized. Once the plunger and syringe combination comes to rest against the impact damper pad at the distal end of the housing, the syringe assembly remains stationary and the plunger begins to move axially forward relative to the syringe. As the plunger moves forward, the pressure within the liquid within the syringe begins to rise rapidly until it reaches a critical threshold pressure. Upon reaching the threshold pressure, a rigid disk separating the first liquid chamber from the second dry drug chamber disengages from a circumferential seal holding it into place relative to the syringe. Once separated from the circumferential seal, the disk moves forward until it comes to rest against a retaining surface in the dry drug chamber and the liquid flows through apertures around the disk and into the dry drug chamber.

If the dry drug chamber contains a dry medicine, the dry medicine is drawn into solution by the liquid as the plunger continues its forward movement and the liquid is forced through the dry drug compartment and into the entrance to the hypodermic needle. Otherwise, the liquid medicine flows through the same chamber and continues on into the recipient. When the liquid is discharged, the coupling that engages the driver spring and the plunger comes into contact with a splitter which disengages the driver spring from the plunger. Without the influence of the driver spring upon the plunger and syringe combination, the energized return spring forces the plunger and syringe combination to retreat rearward towards the proximal end of the device until the hypodermic needle is fully retracted into the housing.

BRIEF DESCRIPTION OF THE DRAWINGS

FIG. 3 provides additional details of the actuation button assembly. FIG. 3A shows the button assembly removed from the housing. FIG. 3B shows the button assembly in place in the housing.

BEST MODE FOR CARRYING OUT THE INVENTION

It is important to note that although the following description will be defined in the context of the example of the preferred embodiment, this is for illustrative purposes only. The invention is not so limited and is applicable to all other embodiments as allowed by the claims.

Figures 1, 1A, 1B:
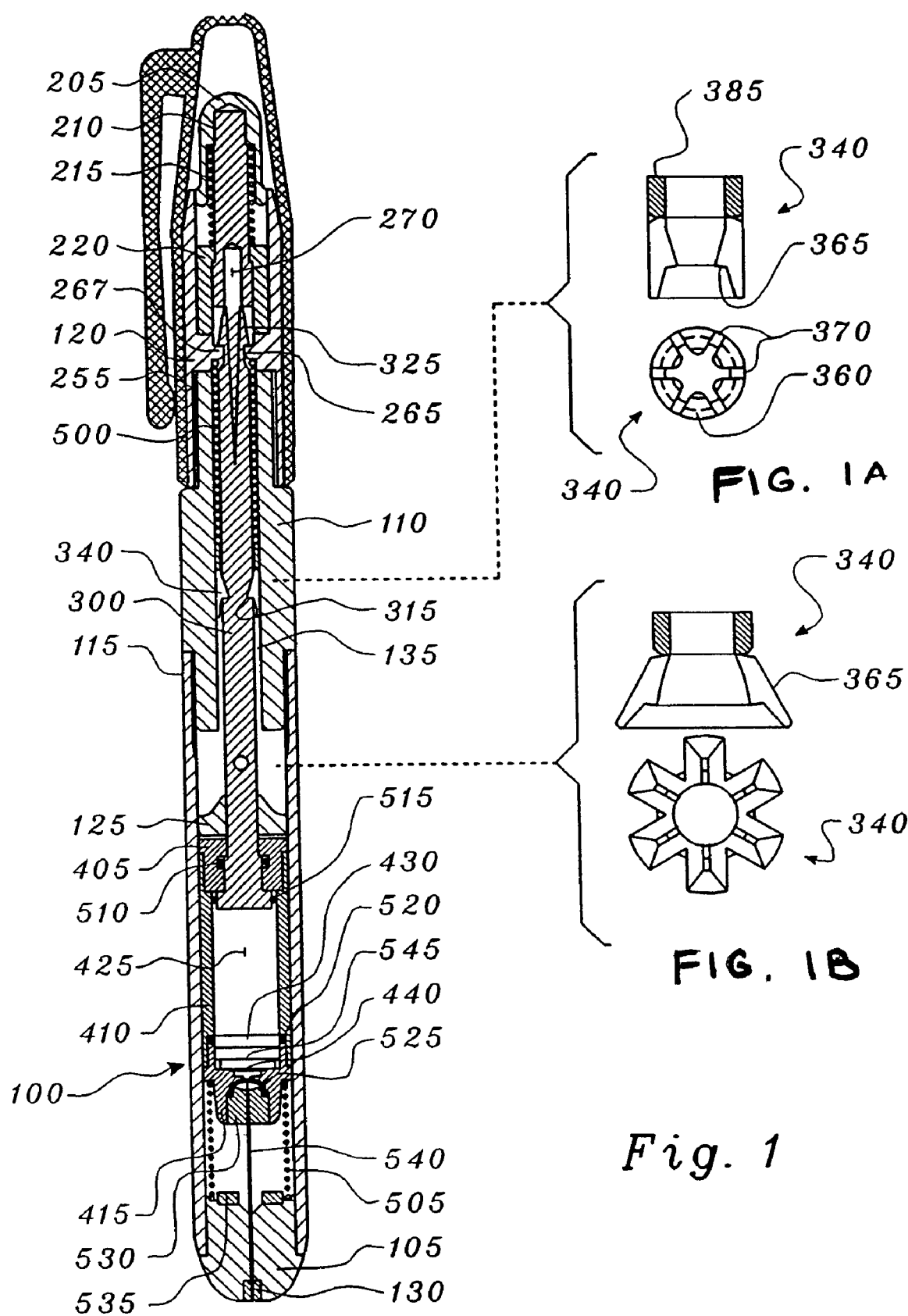
FIG. 1 is a cross-sectional view of a preferred embodiment of the preferred embodiment in a state of readiness.
FIG. 1A shows the spring-plunger coupling in its initial, unexpanded state.
FIG. 1B shows the spring-to-plunger coupling in its expanded state.
Figure 2A:
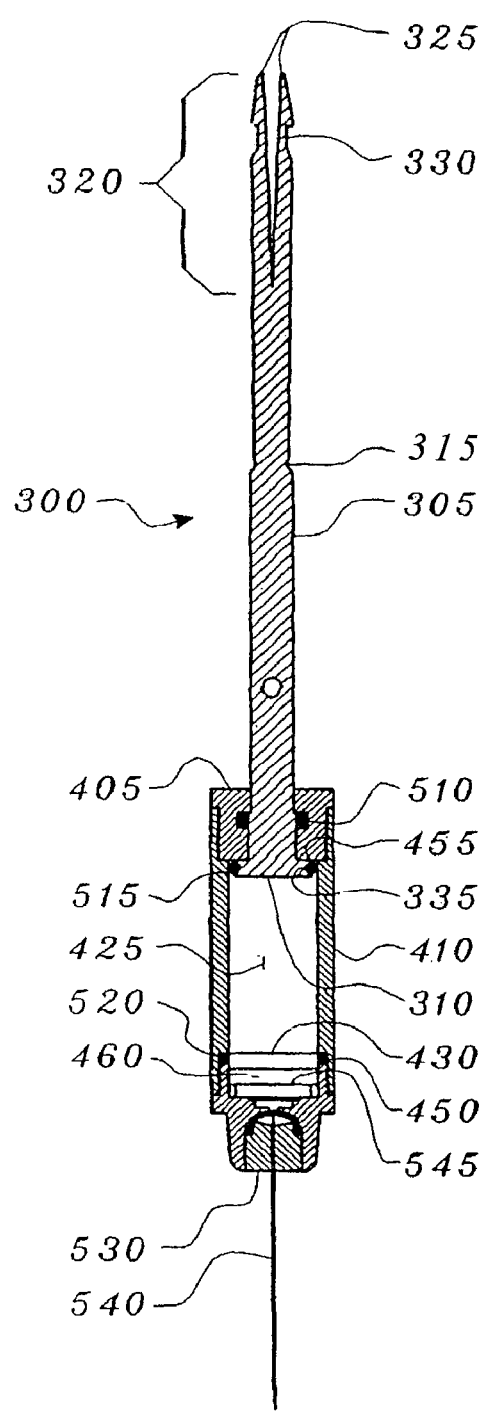
FIG. 2A shows the plunger, syringe and needle assemblies removed from the housing, which is shown in FIG. 2B.
Figure 2B:
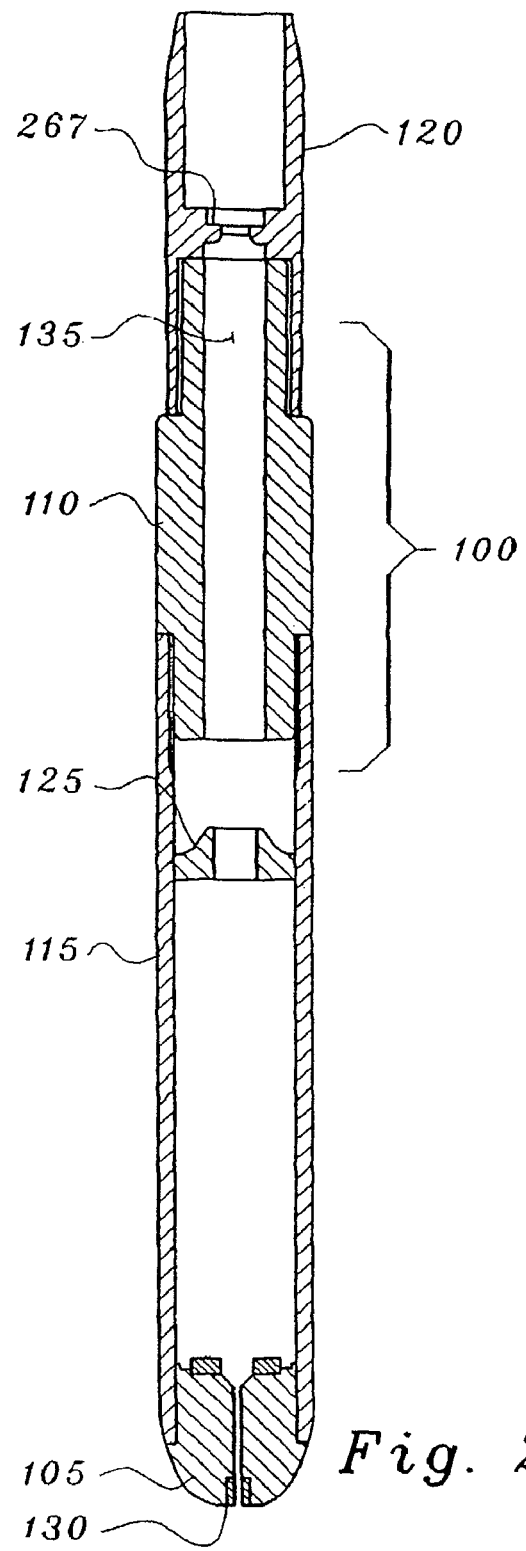
FIG. 2 provides additional details of the housing and plunger, syringe, and needle assemblies.

FIG. 1 shows a cross section of the preferred embodiment of the automatic mixing and injecting apparatus. In this application, "the proximal end" of the apparatus is the end having the actuation button (205), and the "distal end" is the end of the apparatus having the needle (540). The preferred embodiment preferably has a removable cap for preventing accidental triggering, an actuation button (205), an actuation button rod (210), an actuation button return spring (215), an actuation button retainer cap (220), a housing cap (120), a driver spring (500), a spring-to-plunger coupling (340), a housing midsection (110), a plunger (300), a housing tubular section (115), a coupling splitter (125), an upper syringe cap (405), an upper syringe cap seal (510), a plunger seal (515), a liquid medicine, diluent, or solvent, (collectively called "a liquid" (425) hereafter); a syringe barrel (410), a rupture disk (430), a rupture disk seal (520), an optional dry, or lyophilized, medicine (545), a filter (440), a drug chamber lower seal (525), a lower syringe cap (415), a needle hub (530), a needle (540), a syringe return spring (505), an impact damper pad (535), a housing nose (105), and a needle point seal (130). FIG. 2 shows the housing (100), which comprises the housing cap (120), housing midsection (110), housing tubular section (115), and the housing nose (105), which are all permanently joined by means of threaded or bonded connections to form the housing (100).

Referring to FIG. 3, elements (205), (210), (215), (220) and (120) form a permanently assembled actuation button assembly (200). During assembly of the actuation button assembly (200), the actuation button rod (210) enters into axial engagement with the actuation button retainer cap (220) from the distal end of actuation button retainer cap (220). The actuation button rod (210) slidably cooperates with the actuation button retainer cap (220). An exterior radial shoulder (225) exists on the actuation button rod (210) that denotes a sharp reduction, in outside diameter. This shoulder cooperates with a radial shoulder (230) that is interior to the actuation button retainer cap (220) and that defines a transition between the major and minor interior diameters of the actuation button retainer cap (220). The actuation button rod exterior radial shoulder (225) abuts against the actuation button retainer cap (220) interior radial shoulder (230) under the influence of the actuation button return spring (215). This limits the axial travel of the actuation button toward the proximal end of the device.

After the actuation button rod (210) is assembled with the actuation button retainer cap (220), the actuation button return spring (215) slides over the outside of the actuation button rod (210) from the proximal end and rests against the proximal face (235) of the actuation button retainer cap (220). The actuation button (205) is then permanently affixed, preferably by means of press fit, onto the actuation button rod (210). The actuation button return spring (215) is thus captured in a state of minor compression with its distal end resting upon the proximal face (235) of the actuation button retainer cap (220) and the proximal end resting against the interior shoulder (240) of the actuation button (205). After completing the assembly of these elements (205), (210), (215) and (220), the assembly is then permanently assembled, preferably by means of an interference fit, into the proximal end of the housing cap (120).

Following assembly with the housing cap (120), the actuation button (205) slidably cooperates with the interior bore (245) of the housing cap (120) and the actuation button rod (210) slidably cooperates with the interior bore (250) of the actuation button retainer cap (220). When the actuation button (205) is moved axially relative to the housing cap (120) toward the distal end, the actuation button return spring (215) compresses and stores energy. When force against the actuation button (205) is released, the energy stored in the actuation button return spring (215) returns the actuation button (205) and actuation button rod (210) back to a preferred position where the actuation button (205) is extended beyond the proximal end of the housing cap (120) and the shoulder interior radial shoulder of the actuation button rod (210) rests against the interior radial shoulder (230) of the actuation button retainer cap (220).

As shown in FIG. 1, a driver spring (500) is shown in a fully compressed state. The proximal end of the compressed driver spring (500) rests against an interior face (255) of the housing cap (120). The opposite end of the compressed driver spring (500) rests against the proximal surface (385) of the spring-to-plunger coupling (340). In the preferred embodiment, the driver spring (500) stores mechanical energy, and provides an adequate amount of axial extension, to move, upon actuation of the device, the spring-to-plunger coupling (340), and the plunger (300) with which the spring-to-plunger coupling (340) is engaged, axially towards the distal end of the device. This axial movement continues until the spring-to-plunger coupling (340) contacts, and is spread radially by the coupling splitter (125). The before-and-after states of the spring-to-plunger coupling (340) are shown in FIGS. 1A and 1B respectively. In the preferred embodiment, the driver spring (500) retains a residual compressive force at the end of its extension. The driver spring (500) and the spring-to-plunger coupling (340) slidably cooperate with the interior bore (135) of the housing midsection (110).

The spring-to-plunger coupling (340) is captured radially between the interior bore (135) of the housing midsection (110) and a circumferential groove (315) of the plunger (300). In the preferred embodiment, the circumferential groove (315) around the plunger (300) accepts a correspondingly shaped-radial lip (365) on the interior of the spring-to-plunger coupling (340) that allows the compression force of the driver spring (500) applied to the spring-to-plunger coupling (340) to be transmitted axially to the plunger (300). During assembly, the end of the plunger (300) having the barbs (325) is orientated towards the proximal end of the device. The driver spring (500) is then compressed axially between the housing cap (120) and the spring-to-plunger coupling (340), while being captured within the interior bore (135) of the housing midsection (110). This axial compression continues-until the end of the plunger (300) having the barbs (325) contacts the tapered interior surface (260) of the housing cap (120). The plunger (300) of the preferred embodiment is fabricated of a resilient material, which may be metal or plastic, and therefore possesses the capacity for elastic deformation in the barbed region (320). Upon continued compression of the driver spring, the barbs (325) collapse together and pass through an aperture (265) in the housing cap (120) at which time they are elastically deformed. Upon additional compression of the driver spring (500) and further passage of the elastically deformed plunger barbs (325) through the aperture (265) of the housing cap (120), the barbs (325) eventually exit the constraining surface of the housing cap aperture (265). Upon exiting the aperture (265) in a proximal direction, the elastic property of the barbed region (320) allows it to return to its original shape. In the preferred embodiment, the inside diameter of the aperture (265) in the housing cap (120) is slightly smaller than the free distance at the neck (330) of the plunger barbs, thus forming a detent (267) upon which the barbs (325) rest. This insures that the neck (330) of the plunger (300) remains in contact with the aperture surfaces (265) of the housing cap (120), thus insuring the plunger (300) remains centered within the aperture (265) of the housing cap (120) during the device's state of readiness. Once the barbs (325) of the plunger (300) passes through the aperture (265) of the housing cap (120), the driver spring (500) remains in a state of full compression until the actuation button (205) is physically forced towards the distal end of the device.

Figure 4:
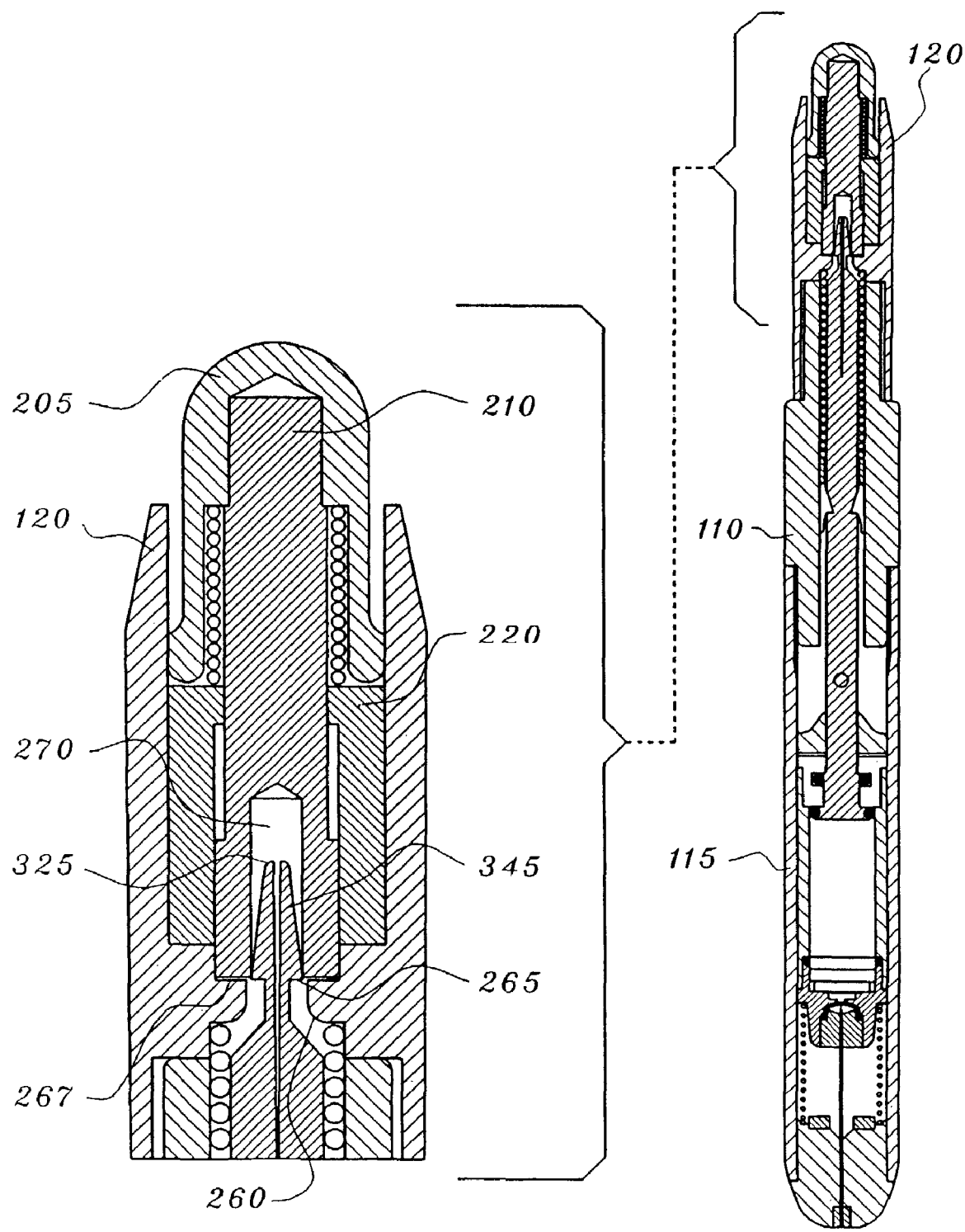
FIG. 4 describes the device, as the actuation button is compressed and just prior to the initial forward movement of the plunger, syringe, and needle assembly.

Referring to FIG. 4, as the user pushes the actuation button (205) towards the distal end of the device, the interior bore (270) of the actuation button rod (210) engages the tapered surface (345) of the plunger barbs (325). Upon continued movement of the actuation button (205), the actuation button rod (210) collects the barbs (325) within the interior bore (270) of the actuation button rod (210), defeating the natural elastic property of the plunger barbed region (320). As the actuation button (205) approaches the limit of its travel in the distal direction, the plunger barbed region (320) is forced together until an interference with the detent (267) no longer exists. Once the plunger barbs (325) compress and the interference condition between the plunger barbs (325) and the housing cap (120) is eliminated, the fully compressed and energized driver spring (500) is no longer constrained from extending in the distal direction. The driver spring extends and forces the plunger towards the distal end of the device by virtue of the circumferential engagement between the plunger (300) and the spring-to-plunger coupling (340) on which the driver spring (500) acts.

As shown in FIG. 2, the plunger (300) has barbs (325), a long cylindrical shaft (305) into which a circumferential groove (315) is machined, and a face (310). The barbs (325) have been previously described. The circumferential groove (315) machined around the periphery of the long cylindrical shaft (305) receives the internally directed radial lip (365) on the interior of the spring-to-plunger coupling (340) as previously described. A circumferential groove (335) is machined about the periphery of the face (310) of the plunger (300). This groove is fitted with an elastomeric plunger seal (515) that resides in contact with, and within the interior confines of, a syringe barrel (410). The plunger seal (515) resides in a state of minor compression between the syringe barrel (410) and the circumferential groove (335) of the face of the plunger (300), and slidably cooperates with the interior surface (420) of the syringe barrel (410). The plunger seal (515) is intended to prevent leakage of the liquid (425) past the plunger (300) as the pressure within the syringe barrel (410) increases. In the preferred embodiment, surfaces of the syringe barrel (410) and plunger (300) that are exposed to direct contact with the liquid (425) would be fabricated of, or coated with, inactive materials which are benign to the human body and are non-reactive with the liquid.

In the preferred embodiment, the syringe barrel (410) is permanently bonded to an upper syringe cap (405). An upper syringe cap seal (510) resides within an interior circumferential groove (445) of the upper syringe cap (405) and resides in a state of compression while resting against the periphery of the plunger (300). At the distal end of the syringe barrel (410), an elastomeric rupture disk seal (520) resides within a cylindrical counterbored pocket (450) where the rupture disk seal (520) makes circumferential and flat contact with the cylindrical counterbored pocket (450) of the syringe barrel.

The flat contact prevents movement of the disk seal (520) if a force in the axial direction towards the proximal end of the device is imposed on the rupture disk seal (520). The inside diameter of the circumferential pocket (450) of the syringe barrel (410) is slightly smaller than the outside diameter of the rupture disk seal (520). The elastomeric rupture disk seal (520) is thus compressed when installed into the counterbored pocket (450) of the syringe barrel (410) and forms a liquid tight seal which prevents the liquid (425) from leaking between the contacting surfaces.

During assembly, the syringe barrel (410) and upper syringe cap (405) are permanently joined, preferably by means of an interference fit. The upper syringe cap seal (510) is then installed in the upper syringe cap (405). The plunger (300) and the plunger seal (515) are then assembled with the syringe barrel (410) and the upper syringe cap (405) with the barbs (325) of the plunger (300) entering the syringe barrel (410) from the distal end of the syringe barrel (410). The plunger (300), then moves axially towards the proximal end of the syringe assembly until the plunger (300), abuts against the inside flat surface (455) of the upper syringe cap (405). This condition represents the relationship that exists between the plunger (300) and the syringe assembly (400) when the device is assembled and in a state of readiness for use.

Once the plunger (300), the syringe barrel (410) and the upper syringe cap (405) have been assembled, the entire assembly is orientated vertically with the barbs (325) of the plunger (300) pointing down and the open end of the syringe barrel (410) pointing up. The interior of the syringe barrel is then filled with the liquid (425) up to a point generally level with the flat center line of the rupture disk seal (520).

Figure 5:
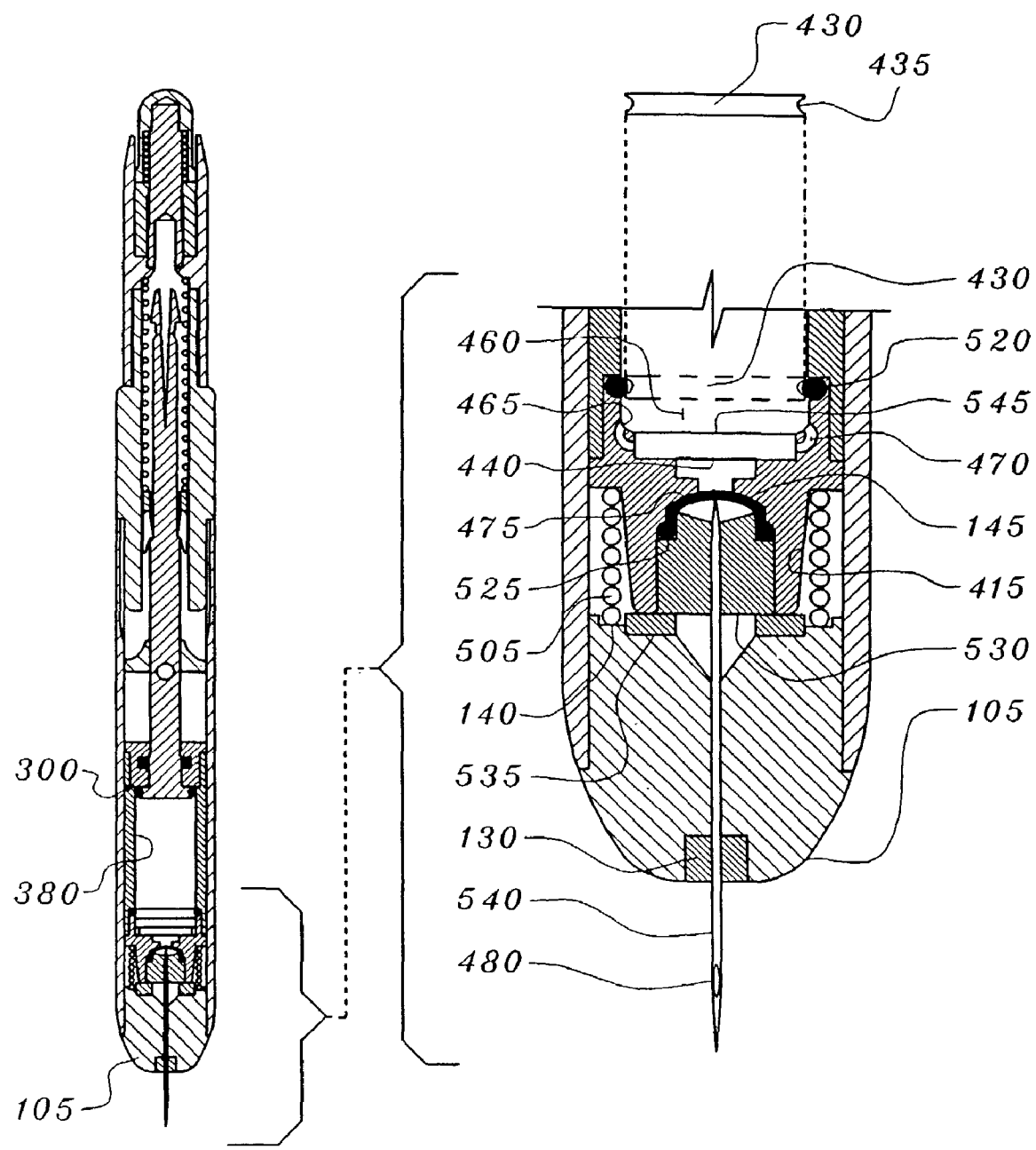
FIG. 5 describes the device as the plunger, syringe, and needle assembly is urged axially into a state where the leading end of the plunger, syringe, and needle assembly comes to rest at the stationary end of the housing and prior to the rigid disk separating from its seal.
Figure 6:
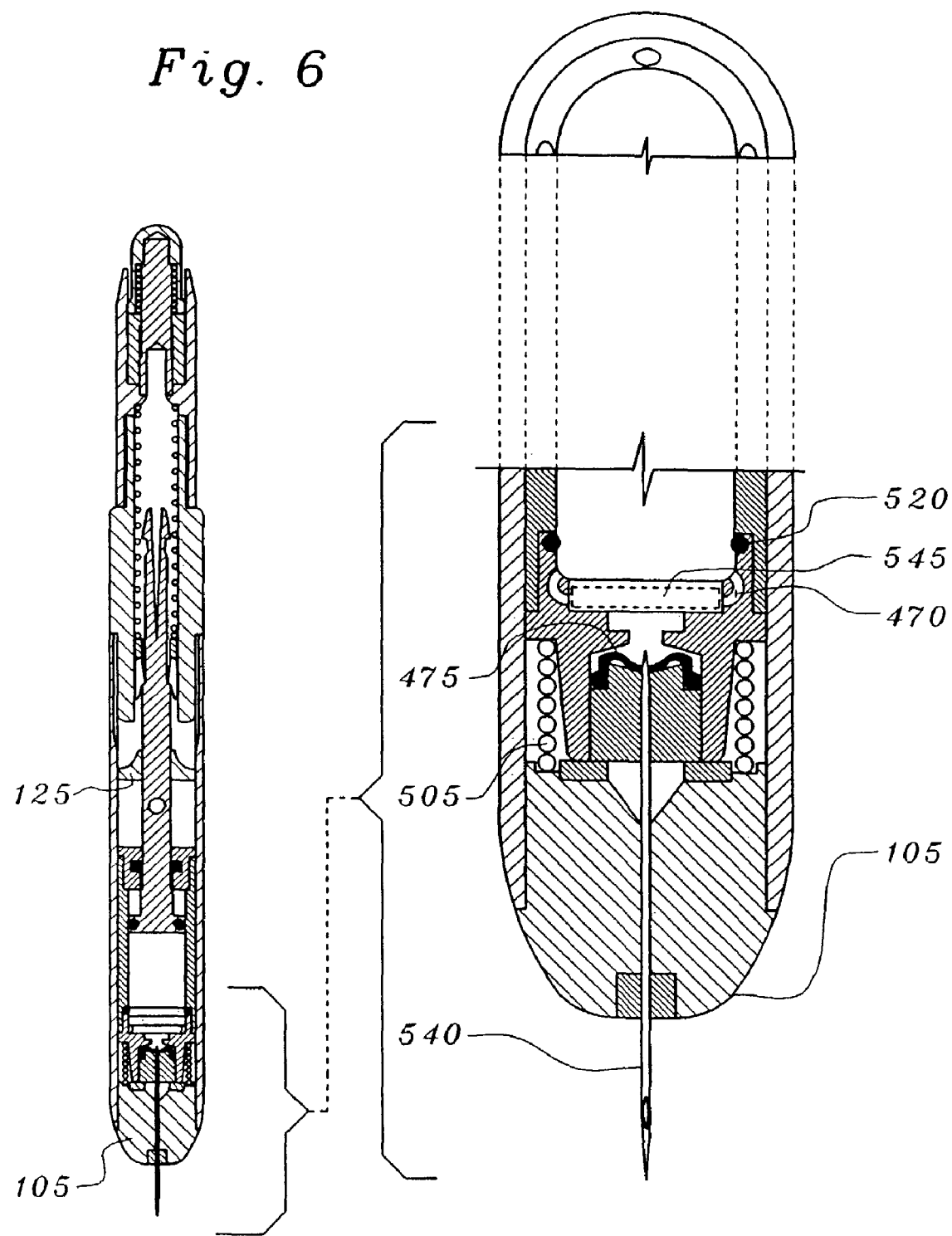
FIG. 6 describes the device as the rigid disk is fully separated from the circumferential seal, the lower drug chamber seal has been penetrated, and as the plunger has commenced its relative movement in relation to the syringe assembly.

Referring to FIGS. 5 and 6, the rupture disk (430) is a thin, generally disk-shaped, non-porous element fashioned with a circumferential groove (435) about its periphery. This circumferential groove (435) is shaped and dimensioned to achieve a secure and elastic interference fit with the disk seal (520) so that the rupture disk seal (520) fits within the peripheral groove (435) of the rupture disk (430) and achieves a compressive fit with it. During assembly, the rupture disk (430) is secured into a compressive, circumferential fit with the rupture disk seal (520) after the rupture disk seal (520) is mounted into position in its designated location within the distal end of the plunger (300) and syringe (400) assemblies and after the syringe barrel (410) is filled with liquid (425). By securing the rupture disk (430) into place within the interior periphery of the rupture disk seal (520) while the rupture disk seal (520) is confined on its exterior within the counterbored pocket (450) of the syringe barrel (410), the rupture disk (430) and disk seal (520) form a fluid-tight barrier preventing air from entering the liquid while also preventing liquid from escaping the syringe barrel.

Once the syringe barrel (410) is loaded with liquid (425) and the rupture disk (430) is assembled with the rupture disk seal (520), the interference fit between the rupture disk exterior and the rupture disk seal interior is adequate to prevent separation of the two under axial loading of the rupture disk until a minimum threshold force is achieved. Assuming the liquid may be generally described as an incompressible fluid, and fluid pressure is applied symmetrically and evenly distributed across the proximal surface of the rupture disk, the internal pressure necessary to separate the rupture disk from the disk seal would be predictable. Once the first chamber is loaded with liquid (425), and the rupture disk (430) is installed, the preferred embodiment may be orientated in any direction.

Separation of the rupture disk (430) from the rupture disk seal (520) occurs at a pressure greater than created by the plunger (300) acting upon the liquid (425) during the free acceleration of the plunger (300) and syringe assembly (400) under the influence of a fully energized driver spring (500). Only after the pressure within the liquid exceeds a predictable threshold under the influence of the plunger (300) will the rupture disk (430) separate from the rupture disk seal (520) and the liquid (425) enter the second, dry drug chamber (460).

As shown in FIG. 5, the lower syringe cap (415) comprises a non-porous element having a proximal cavity to preferably contain a filter (440) and an optional dry or lyophilized medicine (545) and a distal cavity to contain a drug chamber lower seal (525) and a needle hub (530). Once the filter (440) and optional lyophilized medicine (545) are assembled within the proximal cavity of the lower syringe cap (415), the proximal end of the lower syringe cap is fitted within, and is permanently attached to, the distal end of the syringe barrel (410). The lower syringe cap (415) fits within the counter bore in which the rupture disk seal (520) and rupture disk (430) reside. When fully engaged with the syringe barrel (410), the radial surface of the lower syringe cap (415) compresses in the proximal direction against the rupture disk seal (520) and prevents axial movement of the rupture disk seal (520) in the distal direction. The proximal cavity of the lower syringe cap (415) is fashioned to provide a flat surface (465) on which the rupture disk (430) comes to rest when the liquid pressure exceeds the threshold level necessary to separate the rupture disk (430) from engagement with the rupture disk seal (520). The radially disposed interior surface (465) is slightly larger in diameter than outside diameter of the rupture disk (430). At least one aperture (470) across that interior surface (465) is fashioned into the lower syringe cap to allow the liquid to flow past the rupture disk (430) when the rupture disk resides in flat contact with interior surface (465) of the lower syringe cap (415). When the rupture disk (430) resides in this position, the dry drug chamber is effectively divided into a distal portion and a proximal portion, as shown in FIG. 5.

Referring to FIG. 5, a needle (540) is permanently bonded in an axial relationship to a needle hub (530). During final assembly of the syringe (400), an elastomeric drug chamber lower seal (525), which comprises a dome-shaped septum (475) is inserted septum end first into the distal cavity of the tower syringe cap (415) in an axial, proximal direction, until the disk-shaped compression surface of the drug chamber lower seal (525) seats against the receiving surface within the distal cavity of the lower syringe cap (415). Just prior to inserting and seating the drug chamber lower seal (525), the air within the interior of the dry drug chamber (460) (which comprises the space interior to the proximal cavity of the lower syringe cap (415) and enclosed on one end by the rupture disk (430) and on the other end by the drug chamber lower seal (525)), is preferably evacuated.

Once the drug chamber lower seal (525) is installed, the needle (540) and needle hub (530) are then inserted, and permanently affixed into, the lower syringe cap (415), so as to sandwich and compress the sealing surface of the drug chamber lower seal (525) between the flat radial surfaces of the lower syringe cap (415) and the needle hub (530). Once assembled, the proximal end of the needle (540) is positioned close to the concave surface of the drug chamber septum (475). While remaining in an evacuated state, the vacuum within the dry drug chamber (460) pulls the septum (475) of the dry drug lower seal (525) to rest against the distal interior surface of the lower syringe cap (415) so that the only surface on which the vacuum pressure acts is that exposed to the aperture leading from the dry drug chamber (460) to the distal cavity of the lower syringe cap (415).

Referring to FIGS. 1 and 5, at the distal end of the preferred embodiment, the sharp, tissue-penetrating distal end (480) of the needle (540) resides interior to, and in close proximity to, the septum of an elastomeric needle point seal (130). The needle point seal (130) comprises a cylindrical body and a hollow cavity sized slightly larger than the outside diameter of the needle that is open on the proximal end and closed by a thin septum on the distal end. The needle point seal (130) is permanently bonded into a receiving cavity at the distal-most end of the housing nose (105). The needle point seal (130) serves to protect the needle (540) from contamination by sources exterior to the device.

Again referring to FIGS. 1 and 5, the syringe return spring (505) is compressed slightly and positioned so that its axis generally aligns with the long axis of the housing (100). The distal end of the syringe return spring (505) rests upon a radially disposed interior surface (140) of the housing nose (105) and radially exterior to the impact damper pad (535). The proximal end of the syringe return spring (505) rests upon a radially oriented surface (145) proximal to the distal end of the lower syringe cap (415). In the absence of influence by the driver spring (500), the syringe return spring (505) urges the plunger (300) and syringe (400) combination proximally away from the housing nose (105) to a home position with the proximal surface of the upper syringe cap (405) resting against the distal surface (380) of coupling splitter (125). Referring to FIG. 5, the axial distance between the radially disposed and distally facing surface (145) of the lower syringe cap (415) and the interior surface (140) of the housing nose (105) is slightly greater than the solid height of the syringe return spring (505), measured when the distal surface of the lower syringe cap (415) is at rest upon the impact damper pad (535).

FIG. 1 shows the interrelationship between the various elements of the preferred embodiment, in a state of readiness. FIGS. 4 through 9 describe the various states of the device in the order of actuation sequence. FIG. 4 shows the device in an actuated state. FIG. 4 shows an enlarged detail of the proximal end of the device. FIG. 4 shows the actuation button (205) and actuation button rod (210) in an actuated relationship with the energized actuation button return spring (215), the actuation button retainer cap (220), the housing cap (120) and the barbs (325) of the plunger (300). In this view, the actuation button (205) and the actuation button rod (210) are shown at the terminus of their distal travel. Here the barbs (325) of the plunger (300) are shown channeled into the interior bore (270) of the actuation button rod (210).

In FIG. 4, the barbs of the plunger are shown compressed radially inward by the distal movement of the actuation button (205) and the actuation button rod (210) against the tapered surface (345) of the barbs (325). Axial and distal movement of the actuation button rod (210), which is attached to the actuation button (205), defeats the elastic forces urging the two halves of the barbs (325) of the plunger (300) apart. Continued axial and distal movement of the actuation button (205) and actuation button rod (210) relative to the housing cap (120), under the influence of the force imposed on the actuation button (205) by the user, reduces the physical interference between the plunger barbs (325) and the proximal surface of the aperture (265) in the housing cap (120), until, as the actuation button (205) and actuation button rod (210) approach the limit of their axial travel in the distal direction, the physical interference between the plunger and the housing cap ceases.

FIG. 4 thus represents the state when the interference between the plunger (300) and housing cap (120) stops, and just before the plunger (300) begins its acceleration in the distal direction, urged by the fully energized driver spring (500).

FIG. 5 shows the plunger (300) and syringe (400) combination at the end of its travel in the distal direction, where the distal end of the syringe assembly comes to rest against the impact damper pad (535). At this point, the needle (540) is exposed to the furthest extent achievable beyond the distal end of the housing nose (105). As the plunger (300) and syringe (400) combination traverses the distance from its origin to this location, the syringe return spring (505), which is substantially weaker than the driver spring (500), is compressed and gains energy.

As the plunger (300) is disengaged from its interference relationship with the housing cap (120), the fully energized driver spring (500), by virtue of its buttress contact at its proximal end with the interior face (255) of the housing cap (120), and its contact at the distal end at the proximal surface (385) of the spring-to-plunger coupling (340), forces the plunger (300) to accelerate in an axial direction away from the buttressed end of the driver spring (500). The spring-to-plunger coupling (340) is captured radially on its exterior by the interior surface of the interior bore (135) of the housing midsection (110), and radially on the interior by its disengagable interference relationship with the plunger groove (315). This cooperative relationship between the spring-to-plunger coupling (340), the housing midsection (110) and the plunger (300) assures the force of the driver spring (500) is directed to the plunger in a purely axial and distal direction and guides the plunger (300) to travel with its center line coincident to the bore of the housing (100).

Once the plunger (300) and syringe (400) combination comes to rest upon the impact damper pad (535), the force applied to the plunger (300) by the driver spring (500) by means of the spring-to-plunger coupling (340) causes the pressure within the incompressible liquid (425) to rise rapidly, since the liquid (425) is trapped within the syringe barrel. The pressure within the syringe presses on all surfaces equally. As a result, the radial forces cancel each other and the force applied to the liquid (425) by the face (310) of the plunger (300) is transferred to the proximal surface of the rupture disk (430) residing in fluid contact. This pressure is directed in an axial, distal directions perpendicular to the fluid contact surface.

So long as the pressure differential between the proximal side of the rupture disk (430) and the distal side of the rupture disk does not exceed the threshold pressure necessary to dislodge the rupture disk (430) from its circumferential interference engagement with the rupture disk seal (520), the two elements remain engaged. Until the threshold force is exceeded, and the rupture disk separates from the rupture disk seal (520), the force applied to the plunger (300) by the driver spring (500) is applied to the syringe assembly (400) by means of the fluid pressure of the liquid (425) against the rupture disk (430), which in turn acts upon the rupture disk seal (520) that is trapped in axial engagement within the syringe assembly (400). The threshold pressure necessary to dislodge the rupture disk (430) from engagement with the rupture disk seal (520) is made greater than that generated by the plunger (300) acting upon the liquid (425) during the free travel of the syringe assembly (400). By design, the threshold force can only be exceeded once the syringe assembly comes to rest upon the impact damper pad (535) at the end of its allowable travel.

Under the influence of the plunger (300) upon the liquid (425) and the resistance to the imposed force by the securely-engaged rupture disk (430), the plunger (300), and syringe assembly (400) move in tandem in the distal direction. As the syringe assembly (400) begins to move, the distal end (480) of the needle (540) punctures the needle point seal (130) and enters the flesh at the injection site. FIG. 5 shows the preferred embodiment in a state where the needle (540) is fully extended as the syringe assembly (400) contacts the impact damper pad (535) and just prior to the rupture disk (430) separating from engagement with the rupture disk seal (520).

As described in FIG. 6, once the fluid pressure acting upon the rupture disk (430) of the preferred embodiment by the liquid (425) exceeds the threshold amount, the rupture disk (430) disengages from its circumferential interference relationship with the rupture disk seal (520) and moves distally a short distance into physical contact with a proximally-facing surface (465) of the lower syringe cap (415) thin the proximal cavity of the lower syringe cap (415). The supporting surface (465) of the lower syringe cap (415) has an aperture (470) in at least one location, and preferably several locations, to allow the liquid (425) to flow around the rupture disk (430) and into the distal portion of the dry drug chamber (460) where, if the application calls for it, a dry medicine (545) resides.

Once the rupture disk (430) separates from the rupture disk seal (520) and the liquid (425) begins to flood the dry drug chamber (460), the vacuum being maintained within that compartment is broken and the volume within the unit is filled with the liquid (425). If therapeutic application calls for its use, the dry, highly soluble, medicine (545) residing within the dry drug chamber (460) would come into contact with the liquid (425) and rapidly begin to dissolve. Once the entire volume of the dry drug chamber (460) is filled with liquid (425), the pressure rises rapidly under the influence of the plunger (300) moving distally within the syringe barrel (410) and pressing upon the liquid (425). As the pressure rises within the dry drug chamber (460), the pressure, of the liquid (425) causes the septum (475) of the drug chamber lower seal (525), to deflect distally.

As the septum (475) begins to deflect, it pulls away from the interior surface of the lower syringe cap (415) upon which it normally resides, and the surface area of the septum (475) exposed to the liquid expands. This increased surface area allows for an increasing force to act upon the septum (475), which in turn accelerates the distal deflection. The septum (475) eventually begins to invert as depicted in FIG. 6 and comes into penetrating contact with the proximal end of the needle (540), which is preferably beveled to facilitate penetration of the septum (475). When the pressure imposed upon the septum (475) of the drug chamber lower seal (525) exceeds a threshold, the septum (475) becomes fully penetrated by the stationary and securely fixed beveled end of the needle (540) and the liquid (425), possibly mixed with a dry medicine (545), begins to flow out of the needle (540) and into the recipient of the injection.

FIG. 6 depicts the preferred embodiment in a state where the rupture disk (430) is separated from engagement with the rupture disk seal (520), the dry drug chamber (460) within the lower syringe cap (415) is flooded with liquid medicine, the drug chamber septum (475) has been inverted and penetrated by the proximal end of the needle (540) and the plunger (300) is advancing distally causing the liquid medicine to flow through the needle (540) and into the recipient.

Figure 7:
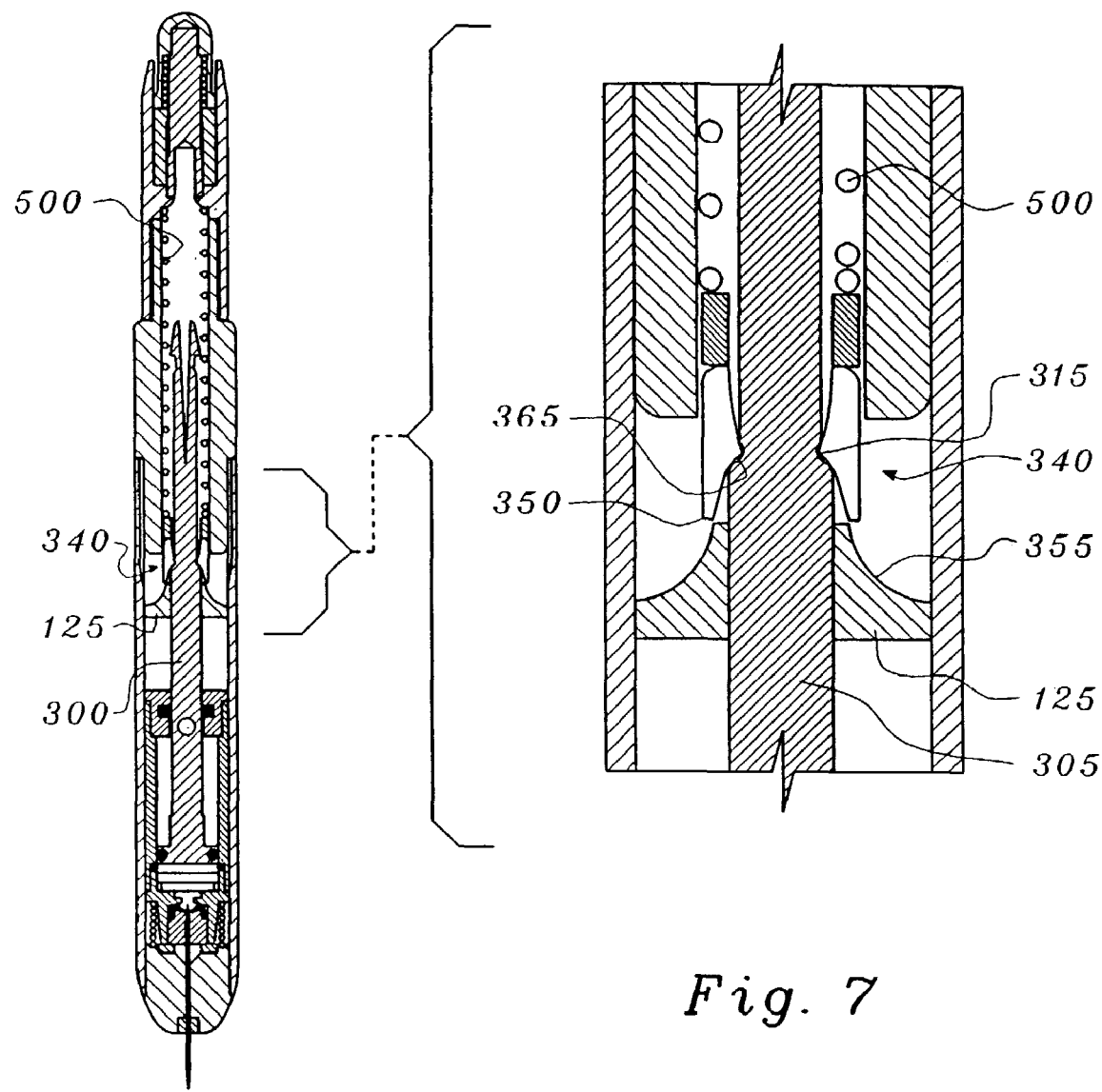
FIG. 7 describes the device when the plunger has moved forward, the injection liquid is almost entirely dispensed, and the leading end of the spring-to-plunger coupling has made contact with the surface of the disengaging element of the housing.

Referring to FIG. 7, as the plunger (300) of the preferred embodiment continues to move distally under the influence of the driver spring (500) by means of the spring-to-plunger coupling (340), the liquid medicine is expelled from the syringe assembly (400) through the needle (540) and into the recipient. As the plunger (300) approaches the distal end of the syringe barrel (410), the distal end (350) of the spring-to-plunger coupling (340) approaches the proximal end of the surface (355) of the coupling splitter (125). This surface (355) is generally sloping from the plunger shaft (305) to a lesser thickness; it may, for example, have a conical cross-section. FIG. 7 describes the state where the volume of liquid (425) dispensed is approaching the volume of the intended dose and spring-to-plunger coupling (340) has initiated contact with the coupling splitter (125).

Figure 8:
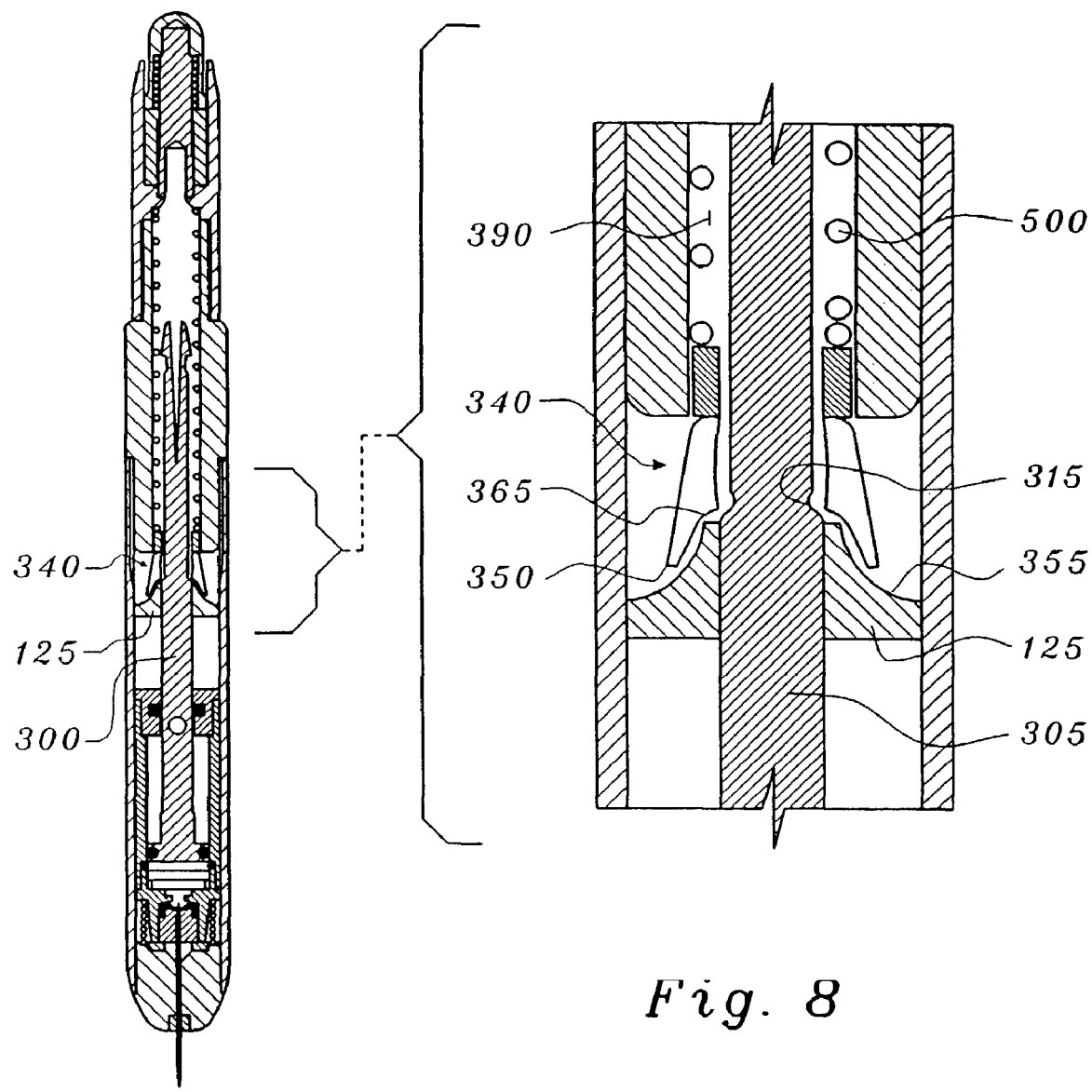
FIG. 8 describes the device as the spring-to-plunger coupling has fully opened and disengaged from the plunger, and the injection liquid has been entirely dispensed, but before the return spring has forced the plunger, syringe, and needle assembly rearward.

Referring to FIGS. 1 and 8, as the injection process nears its conclusion, the plunger (300) of the preferred embodiment continues to move distally under the influence of the driver spring (500) by means of the spring-to-plunger coupling (340) and the distal end (350) of the spring-to-plunger coupling (340) begins to ride over the sloping surface (355) of the coupling splitter (125). The spring-to-plunger coupling (340) is fabricated to include a plurality of axial slits (370) that are equally spaced around its periphery and extend from the distal end to a circumferential groove (360) around the spring-to-plunger coupling (340). The circumferential groove (360) serves to allow for easy flexure of the slotted portion of the spring-to-plunger coupling (340) in the radial direction at a known and axially consistent fulcrum point. The driver spring forces the distal portion (370) of the spring-to-plunger coupling (340) to ride over the surface (355) of the coupling splitter (125). As the slotted portion of the spring-to-plunger coupling (340) begins to open into a rosette pattern in a sliding relation to the sloping surface (355) of the coupling splitter (125), the degree of dimensional interference between the radial lip (365) of the spring-to-plunger coupling (340) and the corresponding groove (315) around the periphery of the plunger (300) diminishes until the engagement between the plunger (300) and the expanded spring-to-plunger coupling (375) ceases altogether.

FIG. 8 describes the state where substantially the entire volume of the liquid (425) has been dispensed, and spring-to-plunger coupling (340) has disengaged entirely from contact with the plunger (300). The driver spring (500) therefore has no further influence on the plunger (300) by way of the spring-to-plunger coupling (340). The interior bore (395) of the spring-to-plunger coupling proximal to the groove (360) is dimensioned to provide an easy slip fit with the shaft (305) of the plunger (300) once the interference relationship between the spring-to-plunger coupling (340) and the plunger (300) is terminated. The flow of medicine out of the syringe barrel (410) ends upon disengagement of the spring-to-plunger coupling (340) from the plunger (300). The plunger (300) and syringe (400) combination is now influenced only by the energized syringe return spring (505) acting upon the distally facing surface (145) of the lower syringe cap (415). FIG. 8 represents the state when the spring-to-plunger coupling has become disengaged from the plunger, and the flow of liquid out of the device has ceased, but the emptied plunger (300) and syringe (400) combination has yet to respond to the influence of the energized syringe return spring (505).

Figure 9:
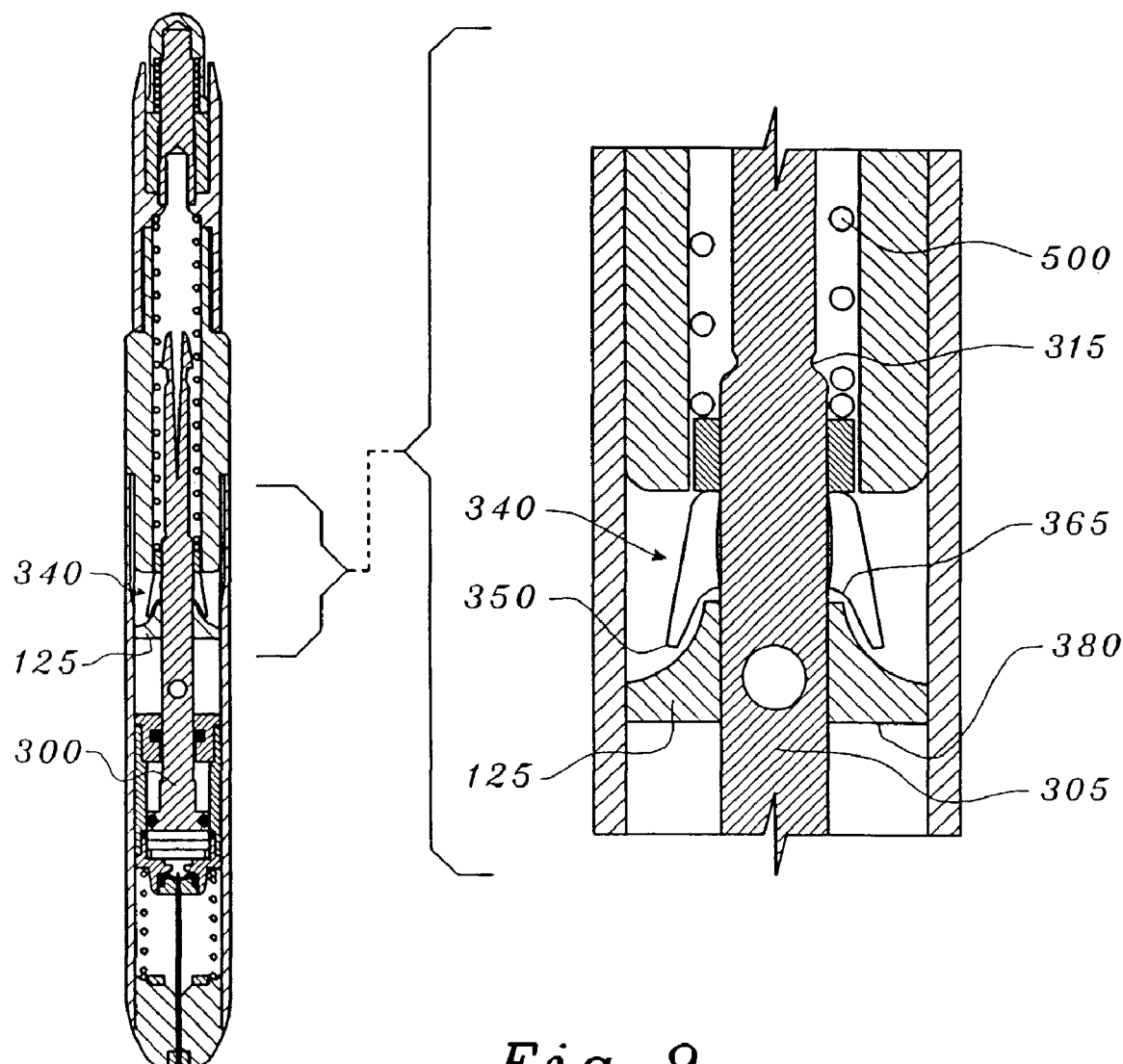
FIG. 9 describes the device when the injection process had completed, and the plunger, syringe, and needle assembly have fully retracted.

As depicted in FIG. 9, once the spring-to-plunger coupling (340) has been flared outward by its involvement with the coupling splitter (125) so as to end its engagement with the plunger (300), and the plunger (300) is therefore no longer urged distally by the driver spring (500), the energized syringe return spring (505) acts upon the lower syringe cap (415), and forces the plunger (300) and syringe (400) combination in a proximal direction. The plunger (300) and syringe (400) combination continues to accelerate in the proximal direction until the proximal surface of the upper syringe cap (405) contacts the distal surface (380) of the coupling splitter (125) at which time the distal end (480) of the needle (540) is fully retracted into the housing nose (105). The syringe return spring (505) remains in a moderately biased and energized state upon full retraction of the plunger (300) and syringe (400) combination.

The device is thus rendered harmless because there is no risk of exposure to the used hypodermic needle and the blood-borne diseases that may be transmitted through contaminated hypodermic needles. The device may then be disposed of by conventional means without risk of injury or infection to others who may come into contact with it. FIG. 9 thus represents the terminal state of the preferred embodiment after the injection process has been completed, the needle has been fully retracted, and the device has been rendered safe for disposal.

I claim:

1. An injection apparatus comprising:
   a first chamber containing a medicine;
   a plunger cooperating with said first chamber, said plunger having a first engaging member defined thereon;
   a needle in fluid communication with said first chamber;
   a coupling having a second engaging member defined in an inner periphery, said first and second engaging members being releasably engaged to one another; and
   a first spring acting on said coupling to urge said plunger in a first direction until said coupling contacts a surface, wherein said surface causes said second engaging member to move radially away from said plunger so that said first and second engaging members are released from one another.

2. The injection apparatus as in claim 1, wherein said first chamber and said needle are movably disposed in a housing.

3. The injection apparatus as in claim 2, further comprising a second spring for urging said first chamber and said needle in a second direction, said second spring being weaker than said first spring.

4. The injection apparatus as in claim 3, wherein said second spring moves said first chamber and said needle in said second direction once said first and second engaging members are released from one another.

5. The injection apparatus as in claim 2, further comprising a damper pad disposed between said housing and said first chamber so that an impact of said first chamber with said housing is dampened.

6. An injection apparatus comprising:
a syringe assembly having a needle, a first chamber for holding a medicine, and a plunger operable to force said medicine from said first chamber through said needle;
a first engaging member being defined on said plunger;
a housing being disposed about said syringe assembly so that said syringe assembly is movable in said housing between a retracted position and an extended position, said housing concealing said needle in said retracted position, and said needle extending from said housing in said extended position;
a first spring for driving said syringe assembly from said retracted position to said extended position and for causing said plunger to drive said medicine through said needle;
a coupling being disposed between said first spring and said plunger, said coupling having a second engaging member, said coupling having a closed position and an open position, said first and second engaging members being engaged to one another when said coupling is in said closed position so that said plunger is drivaebly engaged with said first spring, and said first and second engaging members being disengaged from one another when said coupling opens to said open position so that said plunger is disengaged from said first spring; and
a surface being defined in said housing to open said coupling to said open position from said closed position after said plunger forces said medicine from said first chamber through said needle.

7. The injection apparatus as in claim 6, wherein said surface slopes radially away from said plunger.

8. The injection apparatus as in claim 6, wherein said first engaging member is a groove defined on said plunger and said second engaging member is a lip defined on said coupling.

9. The injection apparatus as in claim 8, wherein said groove is circumferentially defined on said plunger and said lip is circumferentially defined on an inner face of said coupling.

10. The injection apparatus as in claim 6, wherein said coupling further comprises a plurality of openable portions having said second engaging member thereon.

11. The injection apparatus as in claim 10, wherein said first spring drives said plurality of openable portions over said surface to open said portions until said first and second engaging members disengage.

12. The injection apparatus as in claim 6, further comprising a second spring for driving said syringe assembly from said extended position to said retracted position after said coupling is moved to said open position.

13. The injection apparatus as in claim 6, further comprising a damper pad disposed between said housing and said syringe assembly so that an impact of said syringe assembly with said housing when said syringe assembly reaches said extended position is dampened.

14. The injection apparatus as in claim 6, further comprising means for releasably securing said syringe assembly in said retracted position.

15. An injection apparatus comprising:
a housing;
a syringe assembly having a needle, a first chamber for holding a medicine, and a plunger operable to force said medicine from said first chamber through said needle, said syringe assembly being movably disposed in said housing so that said housing conceals said needle in a first position and said needle extends from said housing in a second position;
a first spring for driving said syringe assembly from said first position to said second position and for causing said plunger to drive said medicine through said needle;
a coupling being disposed between said first spring and said plunger, a first portion of said plunger being engaged with a second portion of said coupling when said coupling is in a closed position so that said plunger is drivaebly engaged with said first spring, said first and second portions being disengaged from one another when said coupling opens to an open position so that said plunger is disengaged from said first spring; and
a surface being defined in said housing to open said coupling to said open position from said closed position after said plunger forces said medicine from said first chamber.

16. The injection apparatus as in claim 15, wherein said surface slopes radially away from said plunger.

17. The injection apparatus as in claim 16, wherein said first portion is a groove defined on said plunger and said second portion is a lip defined on said coupling.

18. The injection apparatus as in claim 15, further comprising a second spring for returning said syringe assembly to said first position after said coupling is moved to said open position.

19. The injection apparatus as in claim 15, further comprising a damper pad disposed between said housing and said syringe assembly so that an impact of said syringe assembly with said housing when said syringe assembly reaches said second position is dampened.

20. The injection apparatus as in claim 15, further comprising means for releasably securing said syringe assembly in said first position.

21. An automatic injecting apparatus comprising:
a housing having a cavity and a proximal and a distal end;
a syringe assembly within the housing, the syringe assembly further comprising:
a first chamber for holding a liquid;
a needle; and
a plunger, the plunger having a plunger shaft disposed proximally, the plunger being operable to force the liquid from the first chamber;
the plunger shaft engaging a spring-to-plunger coupling;
a driver spring within the housing, engaging the spring-to-plunger coupling, operable to the syringe assembly to inject the needle and displace the liquid medicine through the needle; and
a splitter formed on the housing distally to the spring-to-plunger coupling; the splitter having a surface for engaging and radially spreading the spring-to-plunger coupling and forcing the spring-to-plunger coupling to disengage from the plunger shaft, thereby disengaging the driver spring from the syringe assembly.

22. The automatic injecting apparatus of claim 21, wherein the plunger shaft further comprises a circumferential groove; and, the spring-to-plunger coupling further comprises:
a plurality of axial slits; and,
a radial lip for releasably engaging the circumferential groove, so that the radial lip disengages from the circumferential groove as the spring-to-plunger coupling engages the splitter.

23. The automatic injecting apparatus of claim 21, further comprising:
a second chamber for holding a liquid;

a disk disposed between the first chamber and the second chamber; the disk releasably sealing the first chamber from the second chamber; and, a least one aperture in the wall of the second chamber allowing liquid communication between the portion of the second chamber proximal to the disengaged disk and the portion of the second chamber distal to the disengaged disk, so that the liquid flows through the second chamber before being forced through the needle.

24. The automatic injecting apparatus of claim 21, further comprising a return spring; the return spring disposed between the housing and the syringe assembly; the return spring urging the syringe assembly proximally when the driver spring is disengaged from the syringe assembly.

25. The automatic mixing and injecting apparatus of claim 21, further comprising:

at least two compressible barbs; the barbs connected to the proximal end of the plunger shaft;

the housing having a housing cap;

a rod disposed within the housing cap; the rod having an interior bore sized to receive the barbs in their compressed state; and, a detent integral with the housing cap; the detent sized to engage the barbs in their uncompressed state and prevent the distal movement of the plunger shaft until the barbs are compressed.

26. The automatic mixing and injecting apparatus of claim 21, further comprising a flexible septum; the flexible septum disposed proximally to the proximal end of the needle and sealing the needle from the second chamber; so that liquid pressure in the chamber causes the septum to deflect distally until the septum is penetrated by the proximal end of the needle.

* * * * *